(12) United States Patent
Kopkalli et al.

(10) Patent No.: US 8,129,574 B2
(45) Date of Patent: Mar. 6, 2012

(54) HYDROGENATION PROCESS FOR FLUOROCARBONS

(75) Inventors: Haluk Kopkalli, Staten Island, NY (US); Yuon Chiu, Denville, NJ (US); Orlando George Rodrigues, Randolph, NJ (US); Gus Cerri, Parsippany, NJ (US); Hsueh Sung Tung, Getzville, NY (US); Stephen A. Cottrell, Baton Rouge, LA (US)

(73) Assignee: Honeywell International Inc., Morristown, NJ (US)

( * ) Notice: Subject to any disclaimer, the term of this patent is extended or adjusted under 35 U.S.C. 154(b) by 0 days.

(21) Appl. No.: 12/550,909

(22) Filed: Aug. 31, 2009

(65) Prior Publication Data
US 2011/0054226 A1 Mar. 3, 2011

(51) Int. Cl.
*C07C 17/00* (2006.01)

(52) U.S. Cl. ........ 570/175; 570/123; 570/124; 570/134; 570/136

(58) Field of Classification Search .......... None
See application file for complete search history.

(56) References Cited

U.S. PATENT DOCUMENTS

| | | | |
|---|---|---|---|
| 4,876,405 A | 10/1989 | Gervasutti | |
| 5,118,888 A | 6/1992 | Gervasutti et al. | |
| 5,396,000 A * | 3/1995 | Nappa et al. ............. | 570/175 |
| 5,679,875 A | 10/1997 | Aoyama et al. | |
| 6,031,141 A | 2/2000 | Mallikarjuna et al. | |
| 6,548,719 B1 | 4/2003 | Nair et al. | |
| 2006/0047170 A1 | 3/2006 | Keggenhoff | |
| 2006/0106263 A1 | 5/2006 | Miller et al. | |
| 2007/0179324 A1 | 8/2007 | Van Der Puy et al. | |
| 2007/0197842 A1 | 8/2007 | Mukhopadhyay et al. | |
| 2008/0000965 A1 | 1/2008 | Shan | |
| 2008/0023175 A1 | 1/2008 | Lehr et al. | |
| 2008/0237090 A1 | 10/2008 | Musich et al. | |
| 2009/0030245 A1 | 1/2009 | Ma et al. | |

FOREIGN PATENT DOCUMENTS

| | | |
|---|---|---|
| EP | 1586370 A2 | 10/2005 |
| WO | 98/33755 A1 | 8/1998 |
| WO | 2008/030440 A2 | 3/2008 |
| WO | 2008/030444 A2 | 3/2008 |
| WO | 2008/054778 A2 | 5/2008 |

* cited by examiner

*Primary Examiner* — Sudhakar Katakam
(74) *Attorney, Agent, or Firm* — Bruce O. Bradford

(57) ABSTRACT

Disclosed is a process and apparatus for the catalytic hydrogenation of fluoroolefins to fluorocarbons where the reaction is carried out in a multi-tube shell and tube reactor. Reactions involving hydrogenation of fluoro-olefins are typically exothermic. In commercial processes where a fluoro-olefin $C_{(n)}H_{(2n-x)}F_{(x)}$ to $C_{(n)}H_{(2n-x+2)}F_{(x)}$ is hydrogenated (e.g. hexafluoropropylene to 236ea, 1225ye to 245eb, and the like), inadequate management or control of heat removal may induce excess hydrogenation, decomposition and hot spots resulting in reduced yields and potential safety issues. In the hydrogenation of fluoro-olefins, it is therefore necessary to control the reaction temperature as precisely as practical to overcome challenges associated with heat management and safety.

9 Claims, 4 Drawing Sheets

Hydrogenation Reactor

HYDROGENATION PROCESS FOR FLUOROCARBONS

FIELD OF THE INVENTION

Fluorocarbons, particularly fluorinated olefins, as a class, have many and varied uses, including as chemical intermediates and monomers. In particular, the hydrogenated products are useful as refrigerants, monomers or intermediates for preparing refrigerants, particularly those identified as having low global warming potential.

BACKGROUND OF THE INVENTION

Several methods for preparing fluorinated olefins are known. Likewise, various reactors for conducting catalytic reactions are known. The following references are cited as non-exclusive examples. These documents are hereby incorporated herein by reference:

U.S. Pat. No. 4,876,405 discloses a process for preparing fluoroethylenes and chlorofluoro-ethylenes from chlorofluoroethanes.

U.S. Pat. No. 5,118,888 discloses a process for the preparation of 1,2-difluoro-ethylene and 1-chloro-1,2-difluoroethylene.

U.S. Pat. No. 5,396,000 discloses a process for producing $CF_3CHFCH_2F$ using vapor phase catalytic dehydrohalogenation to produce $CF_3CF=CHF$ and HF, followed by vapor phase catalytic hydrogenation of $CF_3CF=CHF$ in the presence of HF.

U.S. Pat. No. 5,679,875 discloses methods for manufacturing 1,1,1,2,3-pentafluoropropene (HFO-1225ye) and 1,1,1,2,3-pentafluoropropane (HFC-245eb).

U.S. Pat. No. 6,031,141 discloses a catalytic process using chromium-containing catalysts for the dehydrofluorination of hydrofluorocarbons to fluoroolefins.

U.S. Pat. No. 6,548,719 discloses a process for producing fluoroolefins by dehydrohalogenating a hydrofluorocarbon in the presence of a phase transfer catalyst.

U.S. Publication No. 2006/0106263 discloses the production and purification of hydrofluoroolefin compounds.

U.S. Publication No. 2007/0179324 discloses processes for the production of fluorinated olefins, particularly fluorinated propenes such as the HFO-1234 series.

U.S. Publication No. 2007/0197842 discloses processes for the production of fluorinated olefins including 2,3,3,3-tetrafluoro-2-propene (HFO-1234yf).

U.S. Publication No. 2008/0023175 discloses a method for varying the temperature in a tube bundle reactor for catalytic gas phase reactions.

U.S. Publication No. 2009/0030245 discloses a method for preparing 2,3,3,3-tetrafluoropropene comprising contacting a reactant comprising $CCl_2=CFCH_2Cl$ with a fluorinating agent, such as HF, under conditions effective to produce a reaction product comprising $CF_3CF=CH_2$.

EP Publication No. 1586370 discloses a reactor useful for conducting catalytic gas phase reactions.

PCT Publication No. WO1998/33755 discloses a catalytic process for the dehydrofluorination of hexafluoropropanes to pentafluoropropenes.

PCT Publication No. WO2008/030440 discloses a catalytic process for the preparation of 2,3,3,3-tetrafluoropropene.

PCT Publication No. WO2008/030444 discloses a catalytic process for the preparation of 1,2,3,3,3-pentafluoropropene.

PCT Publication No. WO2008/054778 discloses a catalytic process for the preparation of 2,3,3,3-tetrafluoropropene, a process for producing 1-chloro-2,2,3,3,3-pentafluoropropane and azeotropic compositions of 1-chloro-2,3,3,3-tetrafluoropropene with HF.

Applicants have discovered that the processes of the type described above have disadvantages and/or are not as effective and/or economical as would be practically necessary for large scale commercial production. For example, applicants have come to appreciate that it is generally not possible, by following the teachings of the above references alone, to achieve a process having at once a high degree of ultimate conversion and a high degree of selectivity to the desired fluorinated olefin.

Hydrogenation reactions involving fluoro-olefins are typically highly exothermic. If the heat generated from the reaction is not adequately managed, the high temperatures in the reactor may cause excess hydrogenation, or other side product formation, resulting in reduced yields of the desired product. Therefore, it is necessary to control the reaction temperature.

One method traditionally employed in hydrogenation processes is a large recycle of a cooled portion of the reaction product to effect heat transfer in what's commonly referred to as the trickle bed reactor (a fixed bed reactor packed with catalyst). Recycle of reaction product may not always be suitable especially when the reaction product is susceptible to hydrogenation.

For example, in the hydrogenation of HFC-1225ye (1,2,3,3,3-pentafluorpropene), HFC-236ea (1,1,1,2,3,3-hexafluoropropane) is the desired product but HFC-254 (tetrafluoropropane) is an over-hydrogenation side product that is also observed). Similarly, when the latent heat of the reaction product is low, as in fluorocarbons, processing requires large amounts of recycling, thus making the process less economical. Hence, it is desirable to provide an improved process for the hydrogenation of fluoro-olefins in terms of economics, temperature control and overall safety.

SUMMARY OF THE INVENTION

The present invention is directed to a process for the catalytic hydrogenation of fluoro-olefins to fluorocarbons where the reaction is carried out in a multi-tube shell and tube reactor which has been modified as described herein to provide superior performance.

The present invention provides an improved process for the hydrogenation of fluoro-olefins in terms of temperature control, in terms of lower capital investment when compared to the traditional approach of a high product recycle, and in terms of higher product yields.

In one embodiment, the present invention entails the use of a tubular reactor operating isothermally or near-isothermally. A tubular reactor as used herein is essentially a modified "down-flow" vertical shell and tube heat exchanger with multiple tubes filled with catalyst, suspended between two tubesheets with a cone shaped device attached to the bottom tubesheet to support the catalyst and prevent it from dropping out and distributor device or devices on the upper part of the tubes. The multiple tubes are encased in the "shell" which is a chamber for flowing the heat transfer fluid (such as cooling water, tempered water, glycol solution or any other suitable heat transfer medium) on the outside of the tubes.

In a preferred embodiment, the present invention is directed to a method for the hydrogenation of fluorocarbons which comprises the steps of:

(a) providing reactor means for effecting hydrogenation in a tubular reactor comprising one or more reaction tubes in which each of the tubes contains catalyst and wherein one end of each reaction tubes includes a non-flat shaped catalyst support member;

(b) introducing one or more liquid or vaporized fluoro-olefins to the reactor;

(c) introducing hydrogen gas and controlling the hydrogen feed rate to the reactor;

(d) introducing heat transfer medium to the shell side of the reactor for heat removal and maintenance of reactor operation in an isothermal mode; or near isothermal mode (e) reacting in the vapor phase to produce a hydrogenated reaction product; and (f) recovering the reactor effluent and subjecting it to further purification if desired.

Preferably, the non-flat shaped catalyst support member has a conical shape, wherein the conical shaped catalyst support member has a height that is greater than 0.87 times the diameter. Advantageously, the conical shaped catalyst support member further comprises one support plate with multiple cones. Any suitable material of construction (carbon steel, stainless steel, Inconel, or the like) will work. A mesh screen is advantageously employed, with the mesh size being a function of the size of the catalyst particles. The requirements are cone with a minimum 150% open area and a screen over the cone, where the screen is of suitable mesh size. The mesh should retain the catalyst particles, and be sturdy during use.

In a preferred embodiment, the present invention is directed to a shell-and-tube reactor comprising a shell structure and a tubesheet located in the shell structure, wherein the tubesheet comprises one or more one or more reaction tubes in which each of the tubes contains catalyst and wherein one end of each reaction tubes includes a non-flat shaped catalyst support member.

As described below, a preferred non-flat shape for the catalyst support member is a conical or cone shape.

Advantages of the Cone Shaped Support Member

The conical design of the catalyst support member provides a better surface area than a traditional flat support member. This promotes a lower pressure drop due to fines buildup. Also, the conical shape provides a higher surface area compared to most other shapes. For example, the surface area of a hemisphere is $2\pi r^2$, flat is $\pi r^2$ and a cone is $\pi\sqrt{r^2+h^2}$. (Here, r means radius and h means height of a cone). Thus, in a cone when h is greater than 0.87*d (where d is 2r), the surface area of a cone exceeds that of a hemisphere. In addition, the cone shaped support member is easier to fabricate than a hemispherical shaped support member.

As stated above, the conical design of the catalyst support member aids in significantly reducing the buildup of fine material which may result from attrition by allowing the fines to fall through the non-flat surface of the cone or direct the buildup lower while still allowing surface through which reaction gases to flow. As fines build up between the surface of the cone and the inside of the catalyst tube, they will have a tendency to fall over onto the angular side of the cone providing greater potential for it to pass through to the other side. This provides for minimum amount of build-up and is essentially self-cleaning.

The conical design of the catalyst support member provides ease of use. The assembly is fabricated as one plate with multiple cones. It is easy to use since one does not have to support the catalyst in each individual tube. It is removable as one piece when the catalyst needs to be changed out. It is installed as one piece prior to repacking tubes with catalyst.

The conical design of the catalyst support member provides an increase in the on-stream factor. The greater surface area of the conical support member allows longer operating time due to higher surface area availability to pass fines. Otherwise, shut-downs may be required due to high pressure drop which restricts ability to operate at design rates.

Accordingly, the conical design of the catalyst support member works better than traditional flat support members, and it is the preferred embodiment herein. A flat shape will not work as well due to a reduction in the surface area. It should be noted that other non-flat shapes may provide advantages that are not available with a traditional flat support member. These other non-flat shapes are believed to be less advantageous than the conical shape.

DETAILED DESCRIPTION OF THE INVENTION

Figure 1:
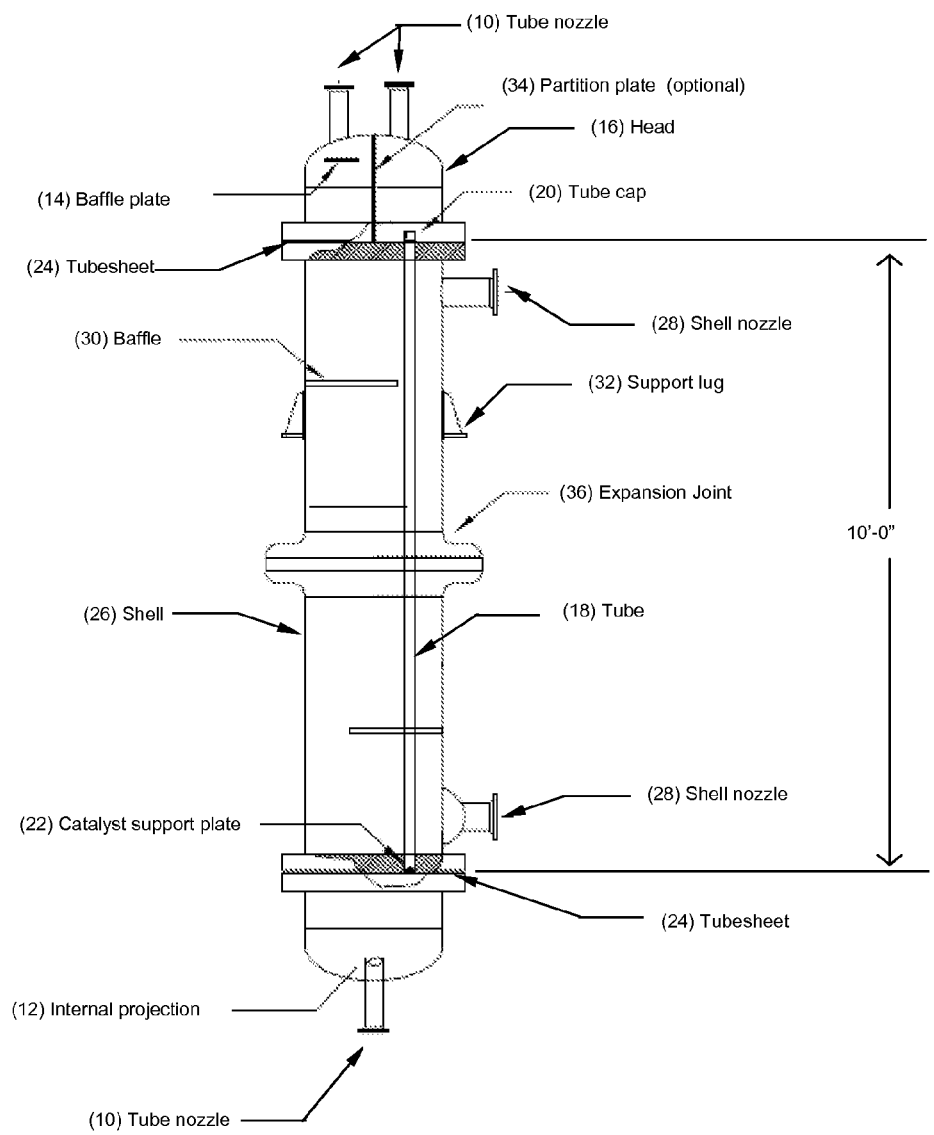
FIG. 1 illustrates one preferred embodiment of a tube and shell reactor useful in the process of the present invention.
Figure 2:
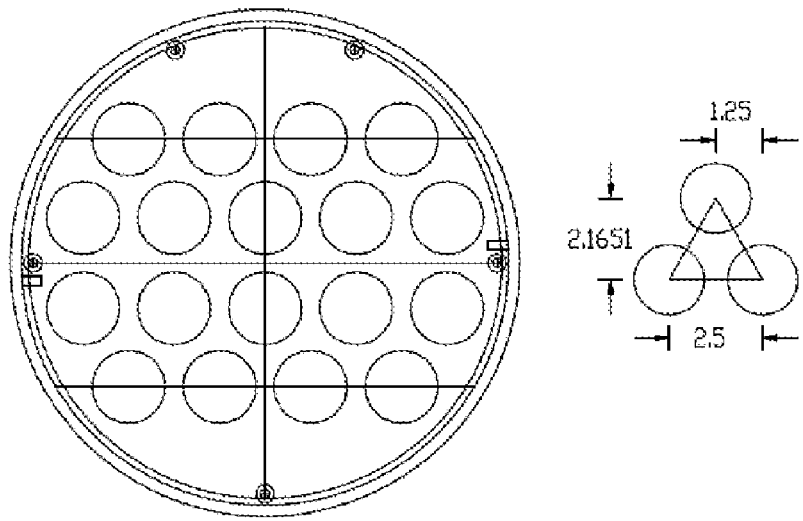
FIG. 2 illustrates one preferred embodiment of the tubesheet layout for the reactor shown in FIG. 1. The triangle shown illustrates the tube pitch.

Referring to the drawings accompanying this disclosure, preferred embodiments of the invention are illustrated as follows:

FIG. 1 shows one embodiment of a tube and shell reactor useful in the process of the present invention. As shown therein, the following component parts are employed:

10—Tube nozzle
12—Internal projection
14—Baffle Plate
16—Head
18—Tube
20—Tube cap
22—Catalyst support plate
24—Tubesheet
26—Shell
28—Shell nozzle
30—Baffle
32—Support lug
34—Partition plate
36—Expansion joint FIG. 2 illustrates a preferred embodiment of the tubesheet layout for the reactor shown in FIG. 1.

The bottom tubesheet should be ground down to a smooth finish. This will allow for a good seal between the tubes (18) holding the catalyst and the catalyst support plate (22).

Figure 3:
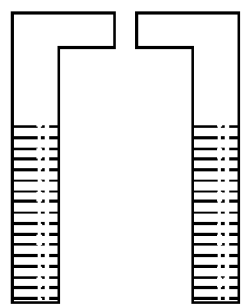
FIG. 3 illustrates one preferred embodiment of tube caps used in the reactor shown in FIG. 1. The tube caps promote uniform distribution of the incoming fluid within the tube, which adds turbulence.

FIG. 3 illustrates one preferred embodiment of tube caps used in the reactor shown in FIG. 1. The tube caps aid in the proper distribution of the incoming fluid within the reactor tubes.

Figure 4:
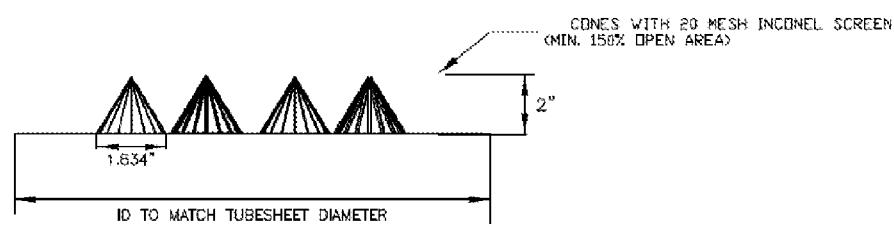
FIGS. 4, 5 and 6 illustrate various views (elevation, isometric & plan, respectively) of one preferred embodiment of the catalyst support plate used in the reactor shown in FIG. 1.
Figure 5:
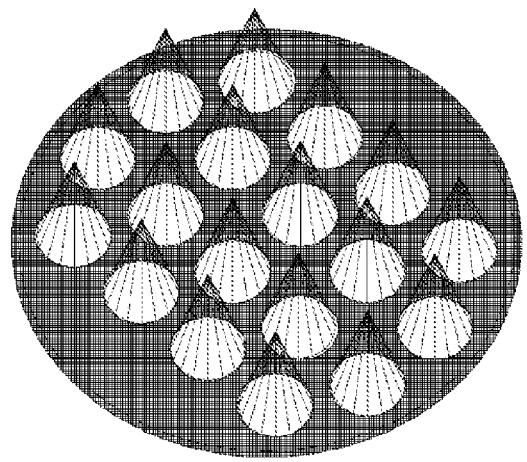
Figure 6:
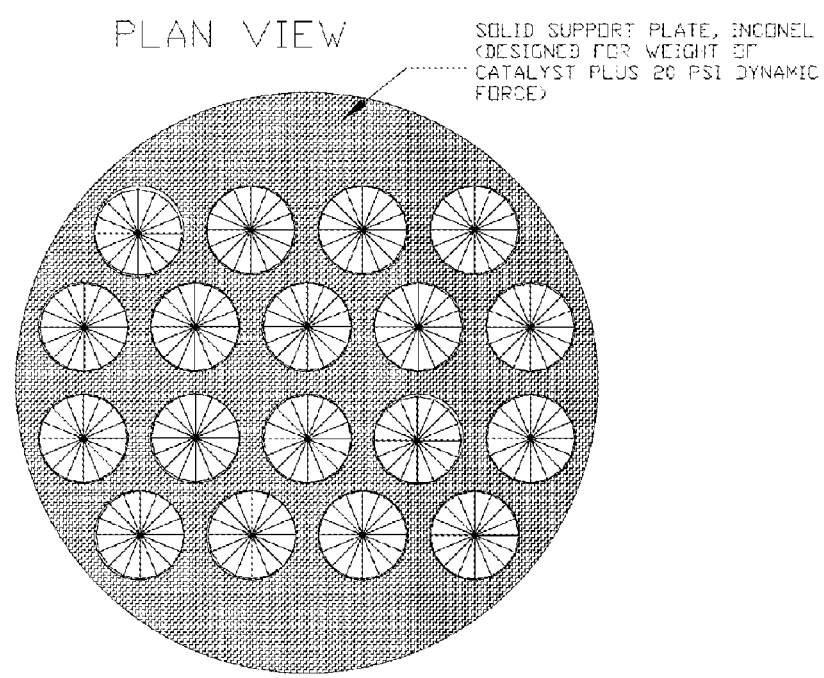

FIGS. 4, 5 and 6 illustrate various views (elevation, isometric & plan, respectively) of one preferred embodiment of the catalyst support plate used in the reactor shown in FIG. 1. As illustrated, this embodiment includes cone-shaped support catalyst members, which provide higher surface area and therefore less pressure drop compared to most other shapes; aid in significantly reducing the build-up of fines due to catalyst attrition and allow for longer run-time as a result of these advantages. Cones are easier to fabricate than, for example hemispherical members which also offer high surface area. In addition, the one-piece nature of the catalyst support plate is easier to install and remove during catalyst change-out and reactor servicing.

As indicated above, the bottom tube sheet should be ground down to a smooth finish. This will allow for a good seal between the tubes (18) holding the catalyst and the catalyst support plate (22). The cone dimensions should be such that each cone will fit inside the individual tubes to retain the catalyst. The catalyst support plate is fastened to the bottom tube sheet with screws or other suitable fasteners.

The dimensions shown in FIGS. 1-6 are reflective of this embodiment of the invention. For a commercial reactor, the diameter could be greater than 10 ft and the number of tubes in the reactor could be in excess of 1,000. In any case, each reactor will include the unique catalyst retention device described herein.

As described above, reactions involving the catalytic hydrogenation of fluoro-olefins are typically exothermic. In commercial processes where a fluoro-olefin $C_{(n)}H_{(2n-x)}F_{(x)}$ to $C_{(n)}H_{(2n-x+2)}F_{(x)}$ is hydrogenated (e.g., hexafluoropropylene to 236ea, 1225ye to 245eb, and the like), inadequate management or control of heat removal may induce excess hydrogenation, decomposition and hot spots resulting in reduced yields and potential safety issues. In the hydrogenation of fluoro-olefins, it is therefore necessary to control the reaction temperature as precisely as practical to overcome challenges associated with heat management and safety.

Particularly useful reactions to make use of this invention include the following:

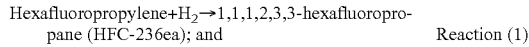

Hexafluoropropylene+$H_2$→1,1,1,2,3,3-hexafluoropropane (HFC-236ea); and        Reaction (1)

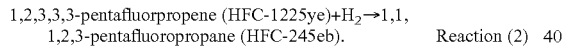

1,2,3,3,3-pentafluoropropene (HFC-1225ye)+$H_2$→1,1,1,2,3-pentafluoropropane (HFC-245eb).        Reaction (2)

Note, an undesired over-hydrogenation product in Reaction (2) is 1,1,1,2-tetrafluoropropane (HFC-254eb).

While the present invention has been particularly shown and described with reference to preferred embodiments, it will be readily appreciated by those of ordinary skill in the art that various changes and modifications may be made without departing from the spirit and scope of the invention. It is intended that the claims be interpreted to cover the disclosed embodiment, those alternatives which have been discussed above and all equivalents thereto.

What is claimed is:

1. A method for the hydrogenation of fluoro-olefins which comprises the steps of:
   (a) providing a reactor for effecting hydrogenation; said reactor consisting of a shell-and-tube reactor having a shell structure and plurality of reaction tubes within the shell structure, wherein each of the reaction tubes contains catalyst, and wherein one end of each reaction tubes includes a cone-shaped catalyst support member mounted on a catalyst support plate; wherein each conical shaped catalyst support member has a height that is greater than 0.87 times the tube diameter;
   (b) introducing one or more liquid or vaporized fluoro-olefins to the reactor;
   (c) introducing hydrogen gas and controlling the hydrogen feed rate to the reactor;
   (d) introducing heat transfer medium to the shell side of the reactor for heat removal and maintenance of reactor operation in an isothermal mode;
   (e) reacting in the vapor phase to produce a hydrogenated reaction product; and
   (f) recovering the reactor effluent and subjecting it to further purification if desired.

2. The method of claim 1, wherein the support plate is connected to the bottom of the tube sheet.

3. The method of claim 2, wherein the bottom of the tube sheet is ground down to a smooth finish.

4. The method of claim 1, wherein the cones of the catalyst support member are covered with a screen of suitable mesh size and have a minimum open area of 150%.

5. The method of claim 4, wherein the cone dimensions are adapted such that each cone will fit inside the individual tubes.

6. The method of claim 1, wherein the reaction tubes further comprise tube caps.

7. A method for the hydrogenation of fluoro-olefins which comprises the steps of:
   (a) providing shell and tube reactor means for effecting hydrogenation in a tubular reactor with the tubes of the reactor filled with catalyst, wherein one end of the tubes include non-flat catalyst support members that provide both high surface area and low pressure drop compared to flat support members; wherein each catalyst support member has a conical shape and has a height that is greater than 0.87 times the tube diameter;
   (b) introducing one or more liquid or vaporized fluoro-olefins to the reactor;
   (c) introducing hydrogen gas and controlling the hydrogen feed rate to the reactor;
   (d) introducing heat transfer medium to the shell side of the reactor for heat removal and maintenance of reactor operation in an isothermal mode or near isothermal mode;
   (e) reacting in the vapor phase to produce a hydrogenated reaction product; and
   (f) recovering the reactor effluent and subjecting it to further purification if desired.

8. The method of claim 7, wherein the cones of the catalyst support member are covered with a screen of suitable mesh size and have a minimum open area of 150%.

9. The method of claim 8, wherein the cone dimensions are adapted such that each cone will fit inside the individual tubes.

* * * * *